(12) United States Patent
Kshirsagar et al.

(10) Patent No.: US 11,497,696 B2
(45) Date of Patent: Nov. 15, 2022

(54) FREE-FLOWING N-ACYL GLYCINATE COMPOSITIONS AT SUB-ZERO TEMPERATURES

(71) Applicant: GALAXY SURFACTANTS LTD., Navi Mumbai (IN)

(72) Inventors: Pooja Vaidya Kshirsagar, Nagpur (IN); Nirmal Koshti, Piscataway, NJ (US); Pramod Bipracharan Sabat, Dombivli (IN)

(73) Assignee: Galaxy Surfactants LTD., Maharashtra (IN)

( * ) Notice: Subject to any disclaimer, the term of this patent is extended or adjusted under 35 U.S.C. 154(b) by 195 days.

(21) Appl. No.: 16/620,760

(22) PCT Filed: Jun. 8, 2018

(86) PCT No.: PCT/IN2018/050380
§ 371 (c)(1),
(2) Date: Dec. 9, 2019

(87) PCT Pub. No.: WO2018/225096
PCT Pub. Date: Dec. 13, 2018

(65) Prior Publication Data
US 2020/0197278 A1 Jun. 25, 2020

(30) Foreign Application Priority Data
Jun. 8, 2017 (IN) .............................. 201721018635

(51) Int. Cl.
*A61K 8/44* (2006.01)
*A61Q 5/02* (2006.01)
*A61Q 19/10* (2006.01)

(52) U.S. Cl.
CPC ............... *A61K 8/44* (2013.01); *A61Q 5/02* (2013.01); *A61Q 19/10* (2013.01)

(58) Field of Classification Search
CPC .... A61K 8/44; A61K 8/442; A61K 2800/596; A61Q 19/10; A61Q 5/02
See application file for complete search history.

(56) References Cited

U.S. PATENT DOCUMENTS

| 9,242,124 | B2 | 1/2016 | Griffin et al. | |
|---|---|---|---|---|
| 2014/0121176 | A1* | 5/2014 | Nadau Fourcade | A61K 8/63 514/33 |
| 2015/0126776 | A1* | 5/2015 | Wang | C07C 231/02 562/575 |

OTHER PUBLICATIONS

Burnett et al; title: Safety Assessment of Amino Acid Alkyl Amides as Used in Cosmetics; International Journal of Toxicology 2017, vol. 36(Supplement 1), pp. 17S-56S. (Year: 2017).*
Regan, et al; title: A Novel Glycinate-based Body Wash Clinical Investigation Into Ultra-mildness, Effective Conditioning, and Improved Consumer Benefits; The Journal of clinical and Aesthetic Dermatology; Jun. 2013, vol. 6, # 6; pp. 23-30. (Year: 2013).*
Ananthapadmanabhan, et al., "Cleansing without compromise: the impact of cleansers on the skin barrier and the technology of mild cleansing", Dermatologic Therapy, vol. 17, pp. 16-25. (2004).
Regan, et al., "A Novel Glycinate-based Body Wash Clinical Investigation Into Ultra-mildness, Effective Conditioning, and Improved Consumer Benefits", The Journal of Clinical and Aesthetic Dermatology, vol. 6, No. 6, pp. 23-30. (Jun. 2013).
Vinardell, et al., "Alternative Methods for Eye and Skin Irritation Tests: An Overview", Journal of Pharmaceutical Sciences, vol. 97, No. 1, pp. 46-59. (Jan. 2008).

* cited by examiner

*Primary Examiner* — Johann R Richter
*Assistant Examiner* — Danielle Sullivan
(74) *Attorney, Agent, or Firm* — Kramer & Amado, P.C.

(57) ABSTRACT

The present invention relates to novel aqueous N-acyl glycinate compositions wherein the said compositions are free-flowing, pumpable, phase-stable on long-term storage, and processable at sub-zero temperatures; more specifically below −5° C. The present invention also relates to the use of these aqueous N-acyl glycinate compositions in preparing isotropic aqueous skin and hair cleansing formulations such as body wash, shower gels, shampoos, and other.

14 Claims, 3 Drawing Sheets

FREE-FLOWING N-ACYL GLYCINATE COMPOSITIONS AT SUB-ZERO TEMPERATURES

FIELD OF INVENTION

The present invention relates to novel aqueous N-acyl glycinate compositions wherein the said compositions are free-flowing at sub-zero temperatures; more specifically at temperature below −5° C. Further, these novel N-acyl glycinate compositions are phase-stable on long-term storage, pumpable, and processable, at sub-zero temperatures. The present invention also relates to the use of these novel aqueous free-flowing N-acyl glycinate compositions in preparing isotropic aqueous skin and hair cleansing formulations such as body wash, shower gels, shampoos, and other.

BACKGROUND OF INVENTION

Surfactants in skin cleansers are designed to remove dirt, sweat, sebum, oil and bacteria from the skin. It is known that interaction of harsh surfactants with stratum corneum (SC) proteins and lipids causes damage to skin, leading to afterwash tightness, dryness, barrier damage, irritation, and even itch. In addition, it leads to a reduction in natural moisturizing factor (NMF) in skin ("Cleansing without compromise: the impact of cleansers on the skin barrier and the technology of mild cleansing." by Ananthapadmanabhan K. P., Moore D. 0.1, Subramanyan K, et al., *Dermatologic Therapy Vol.* 17, 2004, 16-25). Cleanser technology has come a long way from merely cleaning to providing mildness, moisturization, skin & hair sensory, and superior lather. Amino acid-based surfactants are one of those effective mild surfactants providing the above said skin and hair benefiting attributes.

N-acyl glycinates are one of the fundamental amino acid-based surfactants introduced as an essential surfactant by the formulators in their niche products due to its unique properties N-acyl glycinate is an anionic N-acyl glycinate surfactant having the general formula (I)

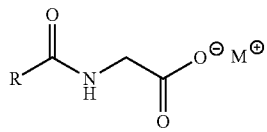

I wherein R is selected from $C_5$ to $C_r$ alkyl group, saturated or unsaturated, and M is a cation selected from $Na^+$ and $K^+$.

N-acyl glycinates are derived from natural coco fatty acid and glycine. Glycine is one of the most abundant amino acids present in the structural proteins (collagen) of human skin and hair. Thus, being compatible to the skin and hair proteins, amino acid-based surfactants especially N-acyl glycinates protect the skin barrier (stratum corneum) function, which rapidly decreases due to loss in Natural Moisturizing Factor (NMF) during cleansing. N-acyl glycinates enhance and protect the intercellular lipids and thus smoothen the skin and hair. Moreover, glycine being the smallest of the naturally occurring amino acids; the charged head group on N-acyl glycinates is significantly smaller than many other surfactants (A Novel Glycinate Based-body Wash: by Jamie Regan., Ananthapadmanabhan K. P., LeonelMaximo Mollica., *The Journal of Clinical and Aesthetic* 2013 June; 6(23-30.) This small size facilitates production of smaller surfactant micelles and the generation of a creamy lather during use. Further, as N-acyl glycinates are prepared from natural occurring coco fatty acid and glycine, they are biodegradable too.

N-acyl glycinates are commercially available most commonly in two different forms i.e. Sodium acyl glycinates and Potassium acyl glycinates. Below is the typical composition of N-acyl glycinates commercially available.

Product Name: Galsoft SCG
INCI: Sodium Cocoyl Glycinate

| | INCI/Chemical Name of components in SCG | CAS No. | Concentration |
|---|---|---|---|
| 1 | Sodium Cocoyl Glycinate | 90387-74-9 | 22% minimum |
| 2 | Sodium chloride | 7647-14-5 | 6% maximum |
| 3 | Water | 7732-18-5 | 73% maximum |

Product Name: Galsoft SLG
INCI: Sodium Lauroyl Glycinate

| | INCI/Chemical Name of components in SLG | CAS No. | Concentration |
|---|---|---|---|
| 1 | Sodium Lauroyl Glycinate | 18777-32-7 | 19% minimum |
| 2 | Sodium chloride | 7647-14-5 | 6% maximum |
| 3 | Water | 7732-18-5 | 73% maximum |

It has been tested that no anionic surfactant other than N-acyl glycinate is near to amphoteric surfactant (betaine) in terms of protein denaturation. A graph showing the results of a Red Blood Cells test done for various surfactants is shown in FIG. 1. Red Blood Cells test is a colorimetric test that correlates surfactant mildness to lack of disruption of the red blood cell membranes. A lower number of % denaturation equates to a milder surfactant (*Alternative Methods for Eye and Skin. Irritation Tests: An Overview*: MP. Vinardell., M. Mitjans., Wiley Interscience., accepted on 16 Nov. 2006). In addition to the less impact on skin proteins, N-acyl glycinates are also less damaging to the skin lipids and hence showcase a broad spectrum mildness on skin and hair.

Being mild, acyl glycinate is one of the best choice for the performance properties in rinse-off formulations, however it comes with a major drawback of higher solidification point i.e. 15° C. Sodium or Potassium salts of acyl glycinate get completely solidify below 15° C. and hence their handling and processing at low temperatures becomes difficult. If acyl glycinates are exposed to low temperatures, they often times get phase separated, and the handling, especially pumping, of acyl glycinates becomes difficult. It becomes non-flowable at temperatures below 15° C. In cases of phase-separated, the end-product formulators have to further process and mix acyl glycinates prior to incorporating it into end-use personal care products such as shampoo, body wash, etc. Globally, it is one of the biggest challenges especially for the countries, where temperature goes below 15° C. in winter. Surfactant industry struggled a lot to provide transportation and processing ease for acyl glycinate compositions. To overcome this handling or processing difficulty of acyl glycinates, temperature controlled tanks (maintained at 25° C.) were designed according to international standards. Thus transportation and processing of acyl glycinates at low temperatures is very tedious and it incurs additional cost for end product formulators. Another approach to resolve transportation/processing and flowability problem in acyl glycinates is to synthesize acyl glycinate compositions with low salt content. Such compositions have low solidification point and are easily processable at temperatures below 0° C. However, such synthesis involves additional step of salt removal, leads to effluent generation which is not an eco-friendly process and has additional cost implication.

To overcome above mentioned difficulties in acyl glycinates, Griffin et. al came up with phase-stable compositions of N-acyl glycinate (U.S. Pat. No. 9,242,124) which teaches "A low-temperature phase-stable concentrate composition consisting of a) an acyl glycinate present in an amount greater than 15 wt %; b) at least one of a zwitterionic surfactant or an amphoteric surfactant present in an amount greater than about 0.1 wt %; and c) water; and, optionally, d) glycerine in an amount from about 0.01 wt % to about 2 wt %; and, optionally, e) at least one electrolyte, wherein the amounts are by total weight of the composition and wherein the concentrate is phase-stable at a temperature less than or equal to 17° C.". Although Griffin et al. has mentioned achieving a low-temperature phase-stable concentrate of acyl glycinates which are phase stable at a temperature less than or equal to 4° C., there is no reference of long term storage stability of those compositions at sub-zero temperatures i.e. at temperatures below 0° C.

Personal care cleansing formulations e.g. shampoo, body wash, etc. contains anionic surfactants as the key active ingredient required to perform cleansing of hair and skin. Anionic activity is another parameter which is important for effective cleansing performance. Anionic surfactant content in these formulations varies from 10-17% active, Presence of amphoteric or non-ionic surfactant or ingredient adversely affect the availability of anionics and thus formulators may struggle to maintain the required anionic content in their formulations to achieve the desired cleansing ability. Griffin et. al have suggested to use at least one zwitterionic or amphoteric surfactant to produce a low-temperature phase-stable N-acyl glycinate composition, thus it reduces overall anionic content of the prior art composition and requires more anionic to be incorporated to achieve the desired anionic content in the formulation.

Accordingly, there is a need for an N-acyl glycinate composition which fulfills the following requirements
1. Free-flowing, pumpable, transportable, phase-stable on long-term storage, processable, at sub-zero temperatures i.e. below 0° C.
2. Provide processing ease for the end formulators without reducing overall anionic content of the composition.
3. Easy to prepare N-acyl glycinate composition without any additional salt removal step, thus cost-effective and no effluent generation.
4. Remains free-flowing, phase-stable even after repeated temperature fluctuations i.e. it is freeze-thaw stable.

SUMMARY OF INVENTION

The present invention provides novel aqueous free-flowing N-acyl glycinate compositions wherein the said composition is pumpable, transportable, phase-stable on long-term storage, processable, at sub-zero temperatures i.e. below 0° C. It can be stored without any deterioration or phase-separation at sub-zero temperatures i.e. at temperature less than −10° C., preferably at less than −5° C., and more preferably less than 0° C.

Accordingly, the present invention relates to aqueous free-flowing N-acyl glycinate composition comprising of:

a) N-acyl glycinate of Formula I present in an amount greater than 17%

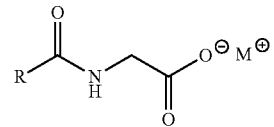

Formula I wherein, R is selected from $C_5$ to $C_{22}$ alkyl group, saturated or unsaturated, and M is a cation selected from $Na^+$ and $K^+$;

b) N-acyl glutamate of Formula II present in an amount of atleast 0.2%

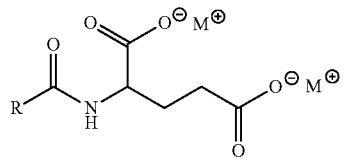

Formula II

Where R is selected from $C_5$ to $C_{22}$ alkyl group, saturated or unsaturated, and M is a cation selected from $Na^+$ and $K^+$;

c) salt in an amount of 6% maximum; and d) water

Wherein the N-acyl glycinate composition is free-flowable at sub-zero temperature i.e. below 0° C.

The present invention also relates to aqueous personal cleansing formulations such as body wash, face wash, shower gels, shampoos, etc. comprising the said novel free-flowing N-acyl glycinate compositions.

OBJECTS OF THE INVENTION (i) It is an objective of the present invention to develop N-acyl glycinates in aqueous form which is free-flowing, pumpable, phase-stable on long-term storage, and processable, at sub-zero temperatures.

ii) it is an objective of the present invention to develop N-acyl glycinates in aqueous form which free-flowing, pumpable, phase-stable on long-term storage, and processable, at less than −10° C.; preferably less than −5° C., more preferably less than 0° C.

iii) It is yet another objective of the present invention to develop an aqueous cleansing skin and hair care composition comprising 1'-acyl glycinates of the present invention, wherein the said skin and hair care composition is isotropic in nature.

BRIEF DESCRIPTION OF THE DRAWINGS

In order to better understand various exemplary embodiments, reference is made to the accompanying drawings, wherein.

DETAILED DESCRIPTION OF INVENTION

Figure 1:
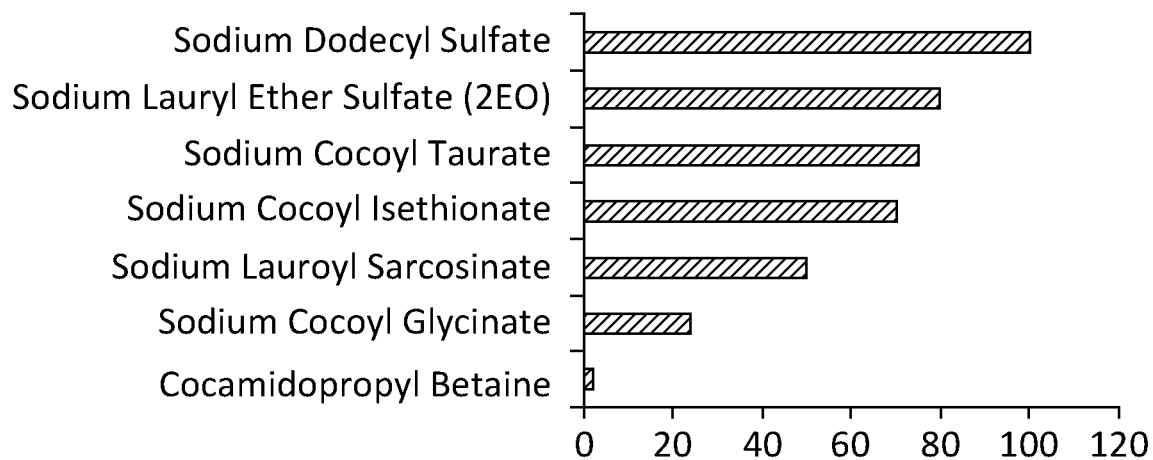
FIG. 1 illustrates the results of a Red Blood Cells test done for various surfactants is shown in FIG. 1.

As explained in the background of the invention, there was a need for aqueous h-acyl glycinate compositions which should remain free-flowing, pumpable, phase-stable on long-term storage, and processable, at sub-zero temperatures i.e. at temperature less than −10° C. preferably at −3 to −5° C., more preferably less than 0° C., and this is achieved through the novel aqueous N-acyl glycinate compositions of the present invention. These novel N-acyl glycinate compositions are important for the countries where temperatures reaches freezing cold in winters.

Although Griffin et al. (U.S. Pat. No. 9,242,124) report a phase-stable composition of N-acyl glycinates, the inventors of the present invention have identified following drawbacks in this prior art.
1. Griffin et al. teaches to use amphoteric or zwitteronic surfactant i.e. it can only be made by using zwitterionic surfactant or amphoteric surfactant like alkyl betaines, alkylamido betaines, and sultaines. Use of zwitteronic, amphoteric surfactant leads to a composition which has anionic content even lower than the commercially available N-acyl glycinates. Thus, it further diminishes available anionic content of the compositions as evident in the comparative examples 9 to 14, and 5A to 10A. Thus, formulators may struggle to maintain the required anionic content in their formulations to achieve the desired cleansing ability.
2. The N-acyl glycinate compositions of the present invention can be stored for extended time period at sub-zero temperatures without any phase separation, unlike the N-acyl glycinate compositions containing amphoteric surfactant which solidifies at sub-zero temperature if stored for extended period of time.
3. The N-acyl glycinate compositions of the present invention are free-flowing at sub-zero temperatures. The comparative examples no. 9 to 14 represents compositions comprising sodium cocoyl glycinate and cocoamidopropyl betaine/sultaines, and examples 5A to 12A represents compositions comprising sodium lauroyl glycinate and cocoamidopropyl betaine/sultaines and it was found that these compositions on long term storage at −5° C. becomes non-flowable.
4. The novel aqueous free-flowing N acyl glycinate compositions of the present invention do not contain any solvent except water; also they do not contain any additional non-surfactant ingredients, whereas Griffin et al. involves addition of glycerin along with zwitterionic surfactant or amphoteric surfactants.

As used herein, the terminology "phase-stable" means that no visible phase separation of acyl glycinate from the aqueous medium is observed at or below a specified ambient temperature. Generally phase-stable system is one in which the system is homogeneous i.e. no phase separation of components.

After further researching on the subject, the inventors of the present invention have unexpectedly found that instead of addition of zwitterionic or amphoteric surfactant, addition of atleast one N-acyl glutamate in N-acyl glycinate results in the product which is free-flowing, having long-term storage phase-stability, processable, transportable, pumpable, even at sub-zero temperatures. Thus, the present invention provides a free-flowing N-acyl glycinate compositions by incorporating atleast one N-acyl glutamate, wherein the aqueous N-acyl glycinates remain flowable, phase-stable, pumpable, transportable, processable at sub-zero temperatures i.e. between 0° C. to −10° C. or even below −10° C. An important aspect of the present invention is that anionic content of this novel N-acyl glycinate composition is not adversely affected or reduced. It was never possible through the teachings of prior art to prepare such aqueous N-acyl glycinate composition having such a high anionic content, and free-flowing, pumpable, phase-stable on long-term storage, transportable; and processable at sub-zero temperatures. Use of N-acyl glutamate has also enabled to achieve better sensory, moisturization and mildness through the compositions of the present invention.

Freeze thaw (sometimes herein referred as "F/T") means a freezing then thawing process. A surfactant composition during the thawing process of a freeze-thaw process often times cannot recover to form the same phase-stable composition as prior to the FIT process: as a result after thawing surfactant composition contains precipitate or becomes hazy or turbid. The term freeze thaw stability or being freeze thaw stable is generally understood to mean that the composition or formulation does not remain gel or contain precipitate after one or more freeze thaw cycle. The phase-stable, free-flowing N-acyl glycinate composition of the present invention is freeze thaw stable; wherein the N-acyl glycinate compositions cooled to down to −15° C. and at 25° C. is recoverable to a homogeneous liquid, (i.e. does not gel or contain precipitate once heated back up to 25° C. or ambient temperature). The free-flowing N-acyl glycinate composition of present invention is freeze thaw stable, also meaning the composition is recoverable to a homogeneous liquid at room temperature after composition is cooled to down to below 2° C., in some cases below 0° C., −5° C., −10° C. and below −15° C. However, in case of N-acyl glycinate compositions containing amphoteric surfactant during thawing process, frozen mass takes longer period of time to return back to homogenous liquid form and further in some cases it does not even regain its original form. The inventors of present invention confirms the faster recovery of the frozen mass of present N-acyl glycinate compositions back to phase stable homogeneous flowable liquid during thawing process. It provides a significant process ease in transportation, loading/unloading in bulk quantities. Further, freeze-thaw is a measure of shelf-life stability of a product and N-acyl glycinate compositions of the present invention passes more than five cycles of freeze thaw which indicates its extended shelf-life at lower temperatures.

Accordingly, the present invention relates to novel aqueous free-flowing N-acyl glycinate composition comprising of:

a) N-acyl glycinate of Formula I present in an amount greater than 17%

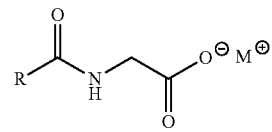

Formula I wherein, R is selected from $C_5$ to $C_{22}$ alkyl group, saturated or unsaturated, and M is a cation selected from $Na^+$ and $K^+$;

b) N-acyl glutamate of Formula II present in an amount of atleast 0.2%

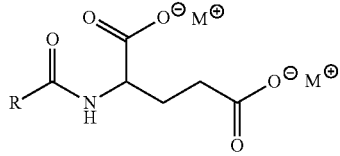

Formula II

Where R is selected from $C_5$ to $C_{22}$ alkyl group, saturated or unsaturated, and M is a cation selected from $Na^+$ and $K^+$;

c) salt in an amount of 6% maximum; and d) water

The present invention also relates to aqueous personal cleansing formulations such as body wash, face wash, shower gels, shampoos, etc. comprising the said novel aqueous phase-stable, free-flowing N-acyl glycinate compositions.

According to an embodiment of the present invention, the total anionic active content of the N-acyl glycinate composition of the present invention is above 23.0%.

In one particular embodiment the N-acyl glycinate is salt of cocoyl glycinate and more typically selected from sodium cocoyl glycinate and potassium cocoyl glycinate. In another particular embodiment the acyl glycinate is lauroyl glycinate salt or more typically selected from sodium lauroyl glycinate and potassium lauroyl glycinate. In a particular embodiment the N-acyl glutamate is cocoyl glutamate salt or more typically selected from potassium cocoyl glutamate and sodium cocoyl glutamate. In another particular embodiment the N-acyl glutamate is lauroyl glutamate salt or more typically from potassium lauroyl glutamate and sodium lauroyl glutamate.

The salt present in the N-acyl glycinate composition of the present invention is a byproduct/impurity carried forward from N-acyl glycinate and N-acyl glutamate generated during the synthesis of said N-acyl glycinate and N-acyl glutamate. The salt is selected from sodium chloride or potassium chloride.

The novel aqueous free-flowing, phase stable compositions of the present invention can be regarded as multifunctional improved N-acyl glycinate surfactant system which is mild, foaming, and capable of moisturization as well. This feature of the cleansing composition is unique because it will help the formulators to create their required personal care/cleansing formulation using their own desired additional ingredients.

The performance characteristics of the present novel aqueous free-flowing N-acyl glycinate compositions are explained as below.

Moisturization:

The aqueous free-flowing N-acyl glycinate compositions of the present invention advantageously provide enhanced moisturization as compared to the composition of Griffin et. al wherein the N-acyl glycinate surfactants are combined with amphoteric/zwitterionic surfactant. On the contrary, inventors of the present invention combines N-acyl glycinate with another amino acid based mild surfactant N-acyl glutamate both are capable of improving water content of the skin and hair.

Sensory Benefits:

Sensory Evaluation is defined as "A scientific discipline used to evoke, Measure, analyze, and interpret those responses to products that are perceived by the senses of sight, smell, touch, taste, and hearing (Stone and Sidel 1993)."

Unlike acyl glycinate compositions containing amphoteric surfactant, the novel free-flowing N-acyl glycinate compositions of present invention provides excellent skin sensorial properties and is illustrated in Example A.

According to an embodiment, the novel aqueous free-flowing N-acyl glycinate compositions of the present invention can be used as a primacy surfactant in the final personal care/cleansing formulation or can be incorporated into personal care/cleansing formulations along with other desired ingredients to prepare shampoos, hand soaps, body washes, face washes, hand washes, shower gels, baby bubble bath, and the like. Hence, formulators of personal care products will find many advantages in using the present inventive aqueous cleansing N-acyl glycinate composition. The present invention does also facilitates to prepare all types of personal care formulations depending upon the need; it is possible to prepare sulfate-free, mild personal cleansing compositions.

Foaming:

Despite the excellent moisturization properties of the present N-acyl glycinate composition, it also demonstrates good creamy foaming. Surprisingly, it has been found that the aqueous cleansing compositions of the present invention exhibits better foam behaviour than commercially supplied N-acyl glycinates of the same concentration and also better than the acyl glycinate compositions containing amphoteric surfactant Addition of N-acyl glutamate even in very small quantity significantly improves foam profile i.e. quantity and quality of foam of N-acyl glycinate. The presence of an excellent foaming effect in aqueous cleansing composition was demonstrated by foam measurements (Hart De George method) as exemplified in Example B.

Advantages (Benefits) of the present invention:

1. The inventive aqueous N-acyl glycinate composition of the present invention is an improved acyl glycinate composition which is free-flowing, pumpable, phase-stable on long-term storage, and processable, at sub-zero temperatures i.e. below 0° C., and can be as low temperature as −10° C. Thus it can be globally transported to any country where temperature reaches sub-zero in the winters.

2. The inventive aqueous free-flowing N-acyl glycinate composition provides equal or high anionic content as compared to commercially available N-acyl glycinates.

3. The inventive aqueous free-flowing N-acyl glycinate composition provides complete anionic content for cleansing which is not possible in the acyl glycinate compositions containing amphoteric surfactant, and moreover the surfactant properties of the inventive N-acyl glycinate composition is further enhanced by the addition of N-acyl glutamate.

4. On thawing, the present N-acyl glycinate composition returns to its isotropic state in short period of time and provides processing ease to the formulator for using it in their final formulations.

5. It shows better foam profile than commercially available N-acyl glycinates.

6. It has better cleansing properties than commercially available N-acyl glycinates.

The inventive aqueous phase-stable N-acyl glycinate composition can also be spray dried and a homogeneous powder is obtained. Thus, the blend of cleansing composition in the dry form can be easily obtained by routine spray-drying operation. Cleansing composition in the solid form can be desired in certain applications where water is to be avoided e.g. solid soap bar.

All the quantities given in percentage (%) are, unless otherwise stated, on the "active matter" basis rather than on the "as is" basis as manufactured. The "active matter" basis, thus, does not include any impurity, by-product, residues, or diluent that may be present in that ingredient/product.

'N-acyl glycinate composition' and 'N-acyl glycinate' both are one and the same and has been used interchangeably in the description of the present invention.

EXAMPLES

TABLE 1

| Product Trade Name | INCI Name | % active |
|---|---|---|
| Galsoft SCG | Sodium Cocoyl Glycinate | 22.50% |
| Galsoft SLG | Sodium Lauroyl Glycinate | 20.70% |

TABLE 1-continued

| Product Trade Name | INCI Name | % active |
|---|---|---|
| Galsoft KCGL | Potassium Cocoyl Glutamate | 29.84% |
| Galsoft SCGL | Sodium Cococyl Glutamate | 21.00% |
| Galaxy CAPB | Cocamidopropyl Betaine | 29.00% |
| Galaxy CAPSB | Cocamidopropyl Sultaine | 40.00% |

Example 1 to 4: Compositions of existing Products commercially available.

Example 5 to 8: Sodium Cocoyl Glycinate Compositions of Present Invention

TABLE 2

Comparative Examples of Sodium Cocoyl Glycinate Compositions

| | Ex. 1 | Ex. 2 | Ex. 3 | Ex. 4 | Ex. 5 | Ex. 6 | Ex. 7 | Ex. 8 |
|---|---|---|---|---|---|---|---|---|
| | | | | % Active | | | | |
| Ingredients: | | | | | | | | |
| Galsoft SCG | 22.5 | — | — | — | 22.14 | 21.82 | 20.92 | 19.8 |
| Galsoft KCGL | — | 29.84 | — | — | 0.5 | 1 | 2 | 3.5 |
| Galaxy CAPB | — | — | 29.0 | — | — | — | — | — |
| Galaxy CAPSB | — | — | — | 40.0 | — | — | — | — |
| Sodium Chloride (NaCl) | 4.95 | — | 5.25 | 6.11 | 4.99 | 4.98 | 4.96 | 5.02 |
| Potassium Chloride (KCl) | — | 5.73 | — | — | — | — | — | — |
| Total % Active | 22.5 | 29.84 | 29.0 | 40.0 | 22.64 | 22.82 | 22.92 | 23.3 |
| Appearance/Properties: | | | | | | | | |
| Initial Appearance at 25° C. | Clear liquid | Clear liquid | Clear liquid | Clear liquid | Clear liquid | Clear liquid | Clear liquid | Clear liquid |
| First Sign of Turbidity (° C.) | 17 | <−10 | <−10 | <−10 | 11 | 9 | <−10 | <−10 |
| Uniform White Liquid (° C.) | 14 | <−10 | <−10 | <−10 | 8 | 5 | <−10 | <−10 |
| Freezing Temperature (° C.) | 13 | <−10 | <−10 | <−10 | −1 | <−10 | <−10 | <−10 |
| Appearance @ freezing temp. | White Solid | Clear Liquid | Clear Liquid | Clear liquid | White Paste | White Paste | Clear Liquid | Clear Liquid |
| F/T Appearance @ RT | Clear/ precip | Clear Liquid | Clear Liquid | Clear liquid | Clear Liquid | Clear Liquid | Clear Liquid | Clear Liquid |

TABLE 3

| | Ex. 9 | Ex. 10 | Ex. 11 | Ex. 12 | Ex. 13 | Ex. 14 |
|---|---|---|---|---|---|---|
| | | | % active | | | |
| Ingredients | | | | | | |
| Galsoft SCG | 21.713 | 20.93 | 19.8 | 21.825 | 21.465 | 20.475 |
| Galsoft KCGL | — | — | — | — | — | — |
| Galaxy CAPB | 1 | 2 | 3.5 | — | — | — |
| Galaxy CAPSB | — | — | — | 1 | 2 | 4 |
| Sodium Chloride (NaCl) | 4.96 | 4.95 | 4.98 | 4.97 | 5.0 | 5.1 |
| Total % Active | 22.713 | 22.93 | 23.3 | 22.825 | 23.465 | 24.475 |
| Appearance/Properties: | | | | | | |
| Initial Appearance at 25° C. | Clear Liquid | Clear Liquid | Clear Liquid | Clear Liquid | Clear Liquid | Clear Liquid |
| First Sign of Turbidity (° C.) | 10 | 8 | <6 | 10 | <6 | <6 |
| Uniform White Liquid (° C.) | 7 | 6 | Clear | 7 | Clear | Clear |
| Freezing Temperature (° C.) | 4 | <4 | <4 | <4 | <4 | <4 |
| Appearance @ freezing temp | White Solid | White Solid | White Solid | White Solid | White Solid | Clear Solid |
| F/T Appearance @ RT | Clear Liquid | Clear Liquid | Clear Liquid | Clear Liquid | Clear Liquid | Clear Liquid |

Example 1A: Sodium Lauroyl Glycinate as commercially available

Example 2A to 4A: Sodium Lauroyl. Glycinate Compositions of the Present Invention

TABLE 4

Comparative Examples of Sodium Lauroyl Glycinate Compositions

| Ingredients | Ex. 1A | Ex. 2A | Ex. 3A | Ex. 4A |
|---|---|---|---|---|
| % Active | | | | |
| Galsoft SLG | 20.7 | 20.286 | 19.458 | 18.216 |
| Galsoft KCGL | — | 0.5968 | 1.8 | 3.5 |
| Galaxy CAPB | — | — | — | — |
| Sodium Chloride (NaCl) | 4.32 | — | — | — |
| Potassium Chloride (KCl) | — | 4.34 | 4.39 | 4.47 |
| Total % Active | 20 | 20.8828 | 21.258 | 21.716 |
| Appearance/Properties: | | | | |
| Initial Appearance at 25° C. | Clear Liquid | Clear Liquid | Clear Liquid | Clear Liquid |
| First Sign of Turbidity (° C.) | 12 | 11 | 3 | <−10 |
| Uniform White Liquid (° C.) | 9 | 8 | 0 to −1 | <−10 |
| Freezing Temperature (° C.) | 5 | 3 | <−10 | <−10 |
| Appearance @ freezing temp | Non-Flowable homogeneous white paste | Non-Flowable homogeneous white paste | Clear Liquid | Clear Liquid |
| F/T Appearance @ RT | Clear/ precipitate | Clear Liquid | Clear Liquid | Clear Liquid |

TABLE 5

Sodium Cocoyl Glycinate Compositions and Sodium Lauryl Glycinate compositions of Present Invention

| | Ex. 5A | Ex. 6A | Ex. 7A | Ex. 8A | Ex. 9A | Ex. 10A |
|---|---|---|---|---|---|---|
| | % active | | | | | |
| Ingredients | | | | | | |
| Galsoft SLG | 20.286 | 20.08 | 19.97 | 20.28 | 19.87 | 19.04 |
| Galsoft KCGL | — | — | — | — | — | — |
| Galaxy CAPB | 0.6 | 0.90 | 1.80 | — | — | — |
| Galaxy CAPSB | 4.25 | — | — | 0.90 | 1.70 | 3.50 |
| Sodium Chloride (NaCl) | — | 4.35 | 4.48 | 4.36 | 4.39 | 4.5 |
| Total % active | 20.886 | 20.98 | 21.77 | 22.36 | 21.57 | 22.54 |
| Appearance/Properties: | | | | | | |
| Initial Appearance at 25° C. | Clear Liquid | Clear Liquid | Clear Liquid | Clear Liquid | Clear Liquid | Clear Liquid |
| First Sign of Turbidity (° C.) | 7.5 | 7 | 0.5 | 7 | 1.5 | −4.5 |
| Uniform White Liquid (° C.) | 5.4 | 4 | −1 | 5 | 0.8 | −5.5 |
| Freezing Temperature (° C.) | <0 | <0 | −4 | −2 | −5 | −7 |
| Appearance @ freezing temp | White Solid | White Solid | White Solid | Crystal/ Solid | Crystal/ Solid | Crystal/ Solid |
| F/T Appearance @ RT | Clear/ precipitate | Clear/ precipitate | Clear/ precipitate | White Solid | White Solid | White Solid |

| | Ex. 1B | Ex. 2B | Ex. 3B | Ex. 4B | Ex. 5B | Ex. 6B |
|---|---|---|---|---|---|---|
| | % Active | | | | | |
| Ingredients | | | | | | |
| Galsoft SCG | — | 21.42 | 20.35 | 19.28 | — | — |
| Galsoft SLG | — | — | — | — | 19.81 | 18.92 |
| Galsoft SCGL | — | 1 | 2 | 3 | 0.9 | 1.8 |
| Sodium Chloride (NaCl) | 3.93 | 4.89 | 4.84 | 4.8 | 4.29 | 4.27 |
| Total % Active | 21 | 22.42 | 22.35 | 22.28 | 20.71 | 20.72 |

-continued

| | Ex. 1B | Ex. 2B | Ex. 3B | Ex. 4B | Ex. 5B | Ex. 6B |
|---|---|---|---|---|---|---|
| | | | % Active | | | |
| Appearance/Properties: | | | | | | |
| Initial Appearance at 25° C. | Clear Liquid | Clear Liquid | Clear Liquid | Clear Liquid | Clear Liquid | Clear Liquid |
| First Sign of Turbidity (° C.) | <−10 | 12 | 6 | <−10 | 10 | 5 |
| Uniform White Liquid (° C.) | <−10 | 9 | 3 | <−10 | 5 | 0 |
| Freeze Temp (° C.) | <−10 | 7 | −5 | <−10 | 2 | −8 |
| Appearance @ Freezing Temperature | Clear Liquid | White Solid | White Solid | Translucent Liquid | White Solid | White Solid |
| F/T Appearance RT | Clear Liquid | Clear Liquid | Clear Liquid | Clear Liquid | Clear Liquid | Clear Liquid |

Performance Benefits Exhibited by the novel free-flowing N-acyl glycinate compositions of the present invention:

Sensory Benefits:

The inventive aqueous free-flowing N-acyl glycinate composition also provides a very good sensory feel to the skin and is illustrated in Example A.

According to an embodiment, the novel aqueous N-acyl glycinate compositions of the present invention can be used directly as a final personal care/cleansing formulation or can be incorporated into personal care/cleansing formulations along with other desired ingredients to prepare shampoos, hand soaps, body washes, face washes, hand washes, shower gels, baby bubble bath, and the like. Hence, formulators of personal care products will find many advantages in using this inventive aqueous cleansing composition.

Example A: Sensory Test

Figure 3:
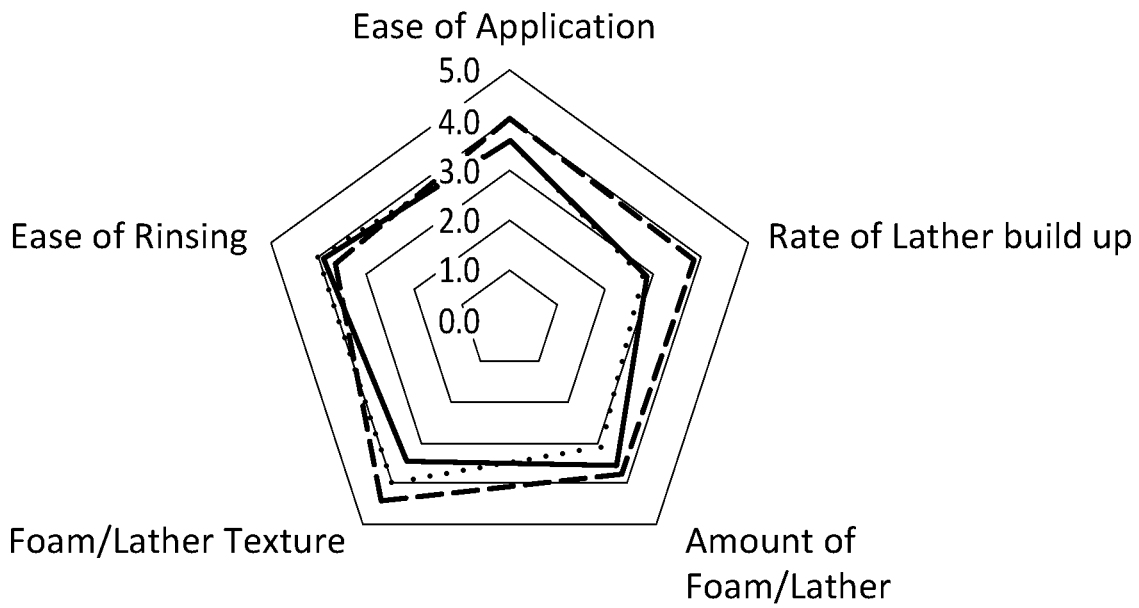
FIG. 3 illustrates the results of a sensory test of surfactant formulations during application and washing.
Figure 4:
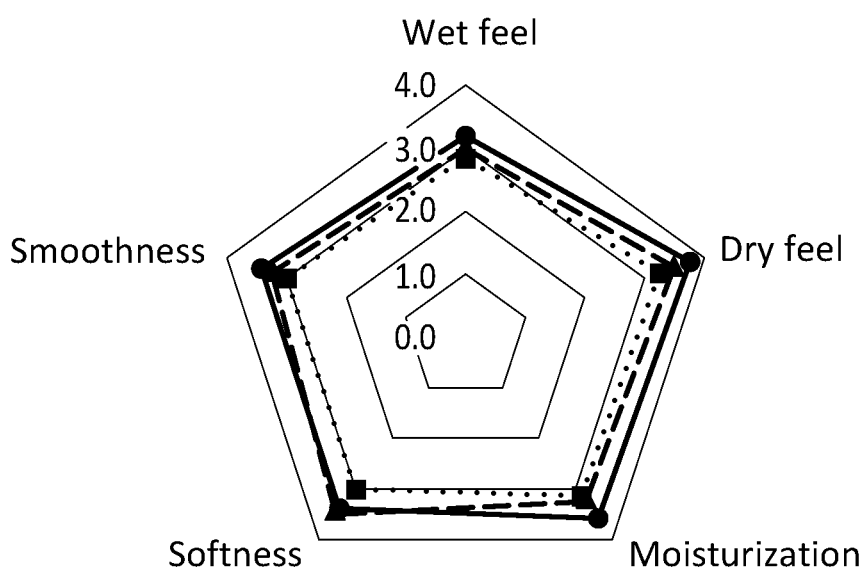
FIG. 4 illustrates the results of a sensory test of surfactant formulations after application.

The inventive aqueous N-acyl glycinate composition also provides a very good sensory feel to the skin. The aqueous composition of Example 8 were compared against Example 11 and Example 1 for sensory test. FIGS. 3 and 4 illustrate the results of the sensory test conducted at different time period of the test. FIG. 3 illustrates the results of the sensory test during application and washing. FIG. 4 illustrates the results of the sensory test after application.

Procedure for Sensory Evaluation:

The test sample was put on the wet palms. This was then applied in circular motion generating lather for 15 seconds Test samples were applied on the wet palms in a circular motion generating lather for 15 seconds. The products was rinsed off under a constant flow of water till the time the subject felt that the product had completely rinsed off Hands were allowed to dry (Towel/'Hand Dryer). Test samples were evaluated on different sensorial parameter. The subjects were asked to compare sensory between the test samples subjectively with the help of questionnaire form.

Each test sample was tried in duplicates to ensure repeatability. The rating scale used is shown in FIG. 2.

Figure 2:
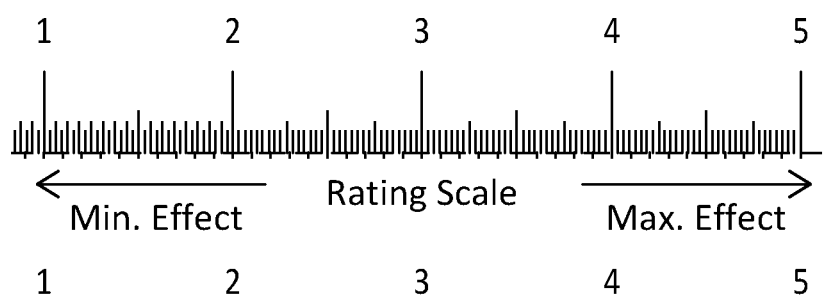
FIG. 2 illustrates a rating scale used for sensory tests of surfactant formulations.

In FIG. 2, scale 1 is the lowest and scale 5 represents the highest performance.

As evident in FIGS. 3 and 4, the inventive composition of Example 8 (SCG/KCGL) is significantly better than Example 11 and Example 1 (Sodium Cocoyl Glycinate).

Example B: Foaming

The foam volume and lather potential of the inventive N-acyl glycinate compositions are substantially higher than the individual surfactants. This synergistic foaming and lather potential of the invention N-acyl glycinate composition of Example 8 was measured and compared with compositions of Example 11 and Example 1.

Foam Volume:

Foam volume was measured as per the below procedure.

1. 100 mL of 1% aqueous solution of (Sodium Cocoyl Glycinate) Example 1 in water having hardness of 150 ppm was used to evaluate the foam volume.
2. The Sodium Cocoyl Glycinate surfactant solution i.e. Example 1 was taken in a kitchen blender and mixed at a speed of 2700 rpm for 60 sec.
3. Foam generated was then collected in the 1000 mL measuring cylinder and the foam volume was measured.

Similarly the above procedure is repeated for composition from. Example 8 and Example 11. The pH of all surfactants solutions were maintained at pH 7. The foam volumes of all surfactants were compared graphically.

Lather Potential:

Lather potential was measured as per the below procedure.

1. 200 mL of 1% aqueous solution of Example 1 in water having hardness of 150 ppm was used to evaluate the lather potential (secs).
2. The surfactant was taken in a kitchen blender and mixed at a speed of 2700 rpm for 60 sec.
3. The foam generated in the kitchen blender was immediately poured through the Lather Potential Assembly (as explained below).
4. The pouring was carried for exactly 15 sec, and waited till the wire was visible. The time from pouring of foam into the funnel until the appearance of the wire reference point, is called lather drainage time or lather potential and is recorded in sec.

Lather Potential Assembly: it consists of a plastic beaker having sieve kept on its mouth. The outer diameter of plastic beaker shall be the same as that of sieve. A funnel is adjusted with the help of a clamp such that its stem bottom rests on the sieve.

Figure 5:
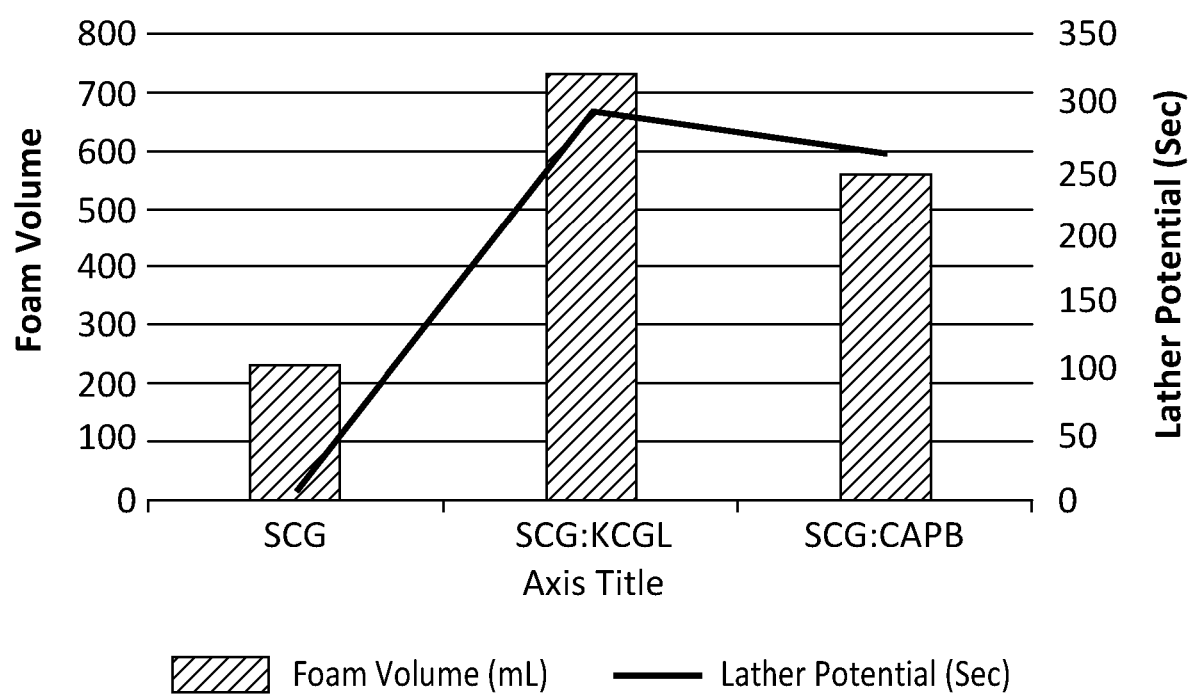
FIG. 5 illustrates foam volume and lather potential of surfactant formulations.

The above procedure was repeated for the inventive composition Example 8 and Example 11. The pH of all surfactants solutions were maintained at pH 7. The lather potential (secs) of all surfactants were compared graphically as mentioned above. As evident in FIG. 5, inventive composition Example 8 (SCG/KCGL) exhibits significantly high lather potential than the Example 1 (SCG) and Example 11 (SCG/CAPB).

We claim:

1. A composition, comprising:
a) an N-acyl glycinate of Formula I, present in an amount of 17% to 23%;

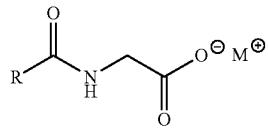
Formula I b) an N-acyl glutamate of Formula II present in an amount of 0.5% to 5%;

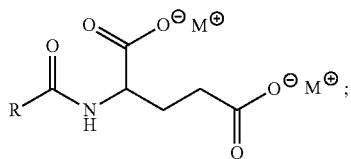
Formula II c) a chloride salt in an amount of less than 6%, wherein the chloride salt is a sodium and/or potassium chloride salt; and
d) water;
wherein:
each R is selected from the group consisting of saturated $C_5$ to $C_{22}$ alkyl groups and unsaturated $C_5$ to $C_{22}$ alkyl groups;
each M is a cation selected from the group consisting of $Na^+$, $K^+$, and a combination thereof; and
the composition is free-flowable at a temperature below 0° C.

2. The composition of claim 1, wherein the N-acyl glycinate is selected from the group consisting of sodium cocoyl glycinate, potassium cocoyl glycinate, sodium lauroyl glycinate, potassium lauroyl glycinate, and a combination thereof.

3. The composition of claim 1, wherein the N-acyl glutamate is selected from the group consisting of sodium cocoyl glutamate, potassium cocoyl glutamate, sodium lauroyl glutamate, potassium lauroyl glutamate, and a combination thereof.

4. The composition of claim 3, wherein the N-acyl glutamate is sodium cocoyl glutamate or potassium cocoyl glutamate.

5. The composition of claim 4, wherein the N-acyl glycinate is sodium lauroyl glycinate, present in an amount of 17% to 22%.

6. The composition of claim 5, wherein:
the N-acyl glutamate is potassium cocoyl glutamate.

7. The composition of claim 5, wherein:
the sodium lauroyl glycinate is present in an amount of 19% to 20.5%; and
the N-acyl glutamate is potassium cocoyl glutamate, present in an amount of 1% to 3.5%.

8. The composition of claim 5, wherein:
the sodium lauroyl glycinate is present in an amount of 17% to 20%; and
the N-acyl glutamate is sodium cocoyl glutamate, present in an amount of 1% to 5%.

9. The composition of claim 1, wherein the salt is sodium chloride, potassium chloride, or a mixture thereof.

10. The composition of claim 1, wherein the N-acyl glycinate composition is free-flowable at a temperature below −5° C.

11. The composition of claim 1, wherein the N-acyl glycinate composition is free-flowable at a temperature below −10° C.

12. A personal care formulation comprising the composition of claim 1.

13. A composition, comprising:
a) an N-acyl glycinate of Formula I, present in an amount of 17% to 22%;

Formula I b) an N-acyl glutamate of Formula II present in an amount of 0.2% to 5%;

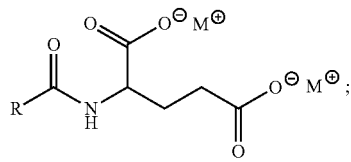
Formula II c) a chloride salt in an amount of less than 6%, wherein the chloride salt is a sodium and/or potassium chloride salt; and
d) water;
wherein:
each R is selected from the group consisting of saturated $C_5$ to $C_{22}$ alkyl groups and unsaturated $C_5$ to $C_{22}$ alkyl groups;
each M is a cation selected from the group consisting of $Na^+$, $K^+$, and a combination thereof; and
the composition is free-flowable at a temperature below 0° C.

14. The composition of claim 5, wherein:
the sodium lauroyl glycinate is present in an amount of 19% to 20.5%; and
the N-acyl glutamate is potassium cocoyl glutamate, present in an amount of 0.5% to 3.5%.

* * * * *